US012734133B2

(12) United States Patent
Mehaffey et al.

(10) Patent No.: US 12,734,133 B2
(45) Date of Patent: Sep. 15, 2026

(54) HIGH OPACITY COATINGS AND SUBSTRATES COATED THEREWITH

(71) Applicant: BPSI HOLDINGS LLC, Wilmington, DE (US)

(72) Inventors: Thomas Mehaffey, Harleysville, PA (US); Manish Ghimire, Harleysville, PA (US)

(73) Assignee: BPSI HOLDINGS LLC, Wilmington, DE (US)

( * ) Notice: Subject to any disclaimer, the term of this patent is extended or adjusted under 35 U.S.C. 154(b) by 387 days.

(21) Appl. No.: 18/260,524

(22) PCT Filed: Jan. 10, 2022

(86) PCT No.: PCT/US2022/011795

§ 371 (c)(1),
(2) Date: Jul. 6, 2023

(87) PCT Pub. No.: WO2022/150693

PCT Pub. Date: Jul. 14, 2022

(65) Prior Publication Data

US 2024/0024247 A1 Jan. 25, 2024

Related U.S. Application Data

(60) Provisional application No. 63/135,931, filed on Jan. 11, 2021.

(51) Int. Cl.
*A61K 9/28* (2006.01)

(52) U.S. Cl.
CPC ............ *A61K 9/2866* (2013.01); *A61K 9/282* (2013.01)

(58) Field of Classification Search
CPC .............................. A61K 9/2866; A61K 9/282
See application file for complete search history.

(56) References Cited

U.S. PATENT DOCUMENTS

| | | | |
|---|---|---|---|
| 4,233,328 | A | 11/1980 | Dawson et al. |
| 6,228,397 | B1 | 5/2001 | Shen et al. |
| 8,968,456 | B2 | 3/2015 | Durig et al. |
| 9,492,395 | B2 | 11/2016 | Schad et al. |
| 10,159,650 | B2 | 12/2018 | Schad et al. |
| 11,191,731 | B2 | 12/2021 | Schad et al. |
| 11,801,205 | B2 | 10/2023 | Sato et al. |
| 12,098,291 | B2 | 9/2024 | Karan et al. |
| 2011/0243997 | A1 | 10/2011 | Asari et al. |
| 2014/0037890 | A1 | 2/2014 | Mcjunkins et al. |
| 2015/0305382 | A1 | 10/2015 | Jelavich et al. |
| 2019/0321300 | A1 | 10/2019 | Schad et al. |
| 2020/0140714 | A1 | 5/2020 | Despax et al. |
| 2020/0224001 | A1 | 7/2020 | Toivonen et al. |
| 2021/0100275 | A1 | 4/2021 | Schad |
| 2021/0259274 | A1 | 8/2021 | Martin |
| 2022/0218619 | A1 | 7/2022 | Takubo et al. |
| 2022/0233450 | A1 | 7/2022 | Escorcia Rodriguez et al. |
| 2022/0347103 | A1 | 11/2022 | Karan et al. |

FOREIGN PATENT DOCUMENTS

| | | | |
|---|---|---|---|
| EP | 3831895 | A1 | 6/2021 |
| WO | 2002003967 | A1 | 1/2002 |
| WO | 2015174868 | A1 | 11/2015 |
| WO | 201920892 | A1 | 1/2019 |
| WO | 2019002170 | A1 | 1/2019 |
| WO | 2019063647 | A1 | 4/2019 |
| WO | 2019102022 | A1 | 5/2019 |
| WO | 2019161408 | A1 | 8/2019 |
| WO | 2020006525 | A1 | 1/2020 |
| WO | 2021062158 | A1 | 4/2021 |
| WO | 2022112519 | A1 | 6/2022 |
| WO | 2023089093 | A1 | 5/2023 |
| WO | 2024189162 | A1 | 9/2024 |

OTHER PUBLICATIONS

International Search Report and Written Opinion for Corresponding International Application No. PCT/US2022/011795, Apr. 4, 2022, 10 pages.
Supplementary European Search Report for Corresponding European Application No. 22737244.8, Sep. 27, 2024, 9 Pages.
Prapai Pradabkham, et al., "Preparation of Aluminium Lakes by Electrocoagulation", Maejo International Journal of Science and Technology, vol. 2, No. 02, pp. 440-443, 2008.
Office Action for Corresponding Japanese Application No. 2023-541719 and English Translation, issued Feb. 12, 2026, 9 pages.

*Primary Examiner* — Robert A Wax
*Assistant Examiner* — Olga V. Tcherkasskaya
(74) *Attorney, Agent, or Firm* — LUCAS & MERCANTI, LLP

(57) ABSTRACT

The present invention is directed film coating compositions for use on oral dosage forms such as compressed tablets and other orally-ingestible substrates which contain a water-soluble polymer, an opacifying agent such as, calcium carbonate or starch, and isomalt. The film coating compositions can be in the form of a fully formulated dry blend or as an aqueous suspension which can be applied either directly to a substrate or after the substrate has been coated with a subcoat. Oral substrates such as tablets coated with the film coating compositions are also disclosed and have high opacity and overall excellent appearance.

22 Claims, No Drawings

HIGH OPACITY COATINGS AND SUBSTRATES COATED THEREWITH

CROSS-REFERENCE TO RELATED APPLICATIONS

This application is a 371 of PCT/US2022/011795, filed Jan. 10, 2022, which claims the benefit of U.S. Provisional Application No. 63/135,931, filed Jan. 11, 2021, the contents of each of which are incorporated herein by reference.

FIELD OF THE INVENTION

The present invention relates to coating formulations which, when coated onto orally ingestible substrates, have high opacity without the inclusion of titanium dioxide. The invention also relates to pharmaceutical and nutritional substrates having such film coatings and methods of preparing the same.

BACKGROUND OF THE INVENTION

Film coatings have been used on orally-ingestible substrates such as pharmaceutical and dietary supplement products for many years. Prior art coating formulations typically contain a polymer, a plasticizer, optional pigments and other additives to improve aesthetics, functional properties or processability. With respect to pigments, both synthetic and natural colorants have been used in film coating formulations. Titanium dioxide has been commonly used as a white pigment and also to provide opacity to a coating formulation so that the underlying color of an orally-ingestible core does not interfere with the intended color of the coating formulation. Presently, there is increasing regulatory scrutiny of titanium dioxide, which has led to an emerging formulation trend to avoid the use of titanium dioxide by some manufacturers of orally-ingestible substrates. Calcium carbonate and starch have been used in some cases as replacements for titanium dioxide. However, the opacity of substitutes for titanium dioxide is much lower than that of titanium dioxide. Therefore, there is a need in the art to enhance the opacity of film coatings which do not include titanium dioxide. The present invention addresses this need.

SUMMARY OF THE INVENTION

It has been surprisingly found that the opacity of film coatings containing opacifying agents such as calcium carbonate and/or starch is significantly enhanced by inclusion of isomalt in the film coating formulation. In one embodiment, the present invention relates to the development of a fully-formulated film coating system comprising isomalt, and calcium carbonate. In a separate embodiment, the invention relates to film coating system containing isomalt and starch. Still further embodiments of the invention include film coating compositions containing isomalt, and fine particle size grades of microcrystalline cellulose (MCC) or combinations of opacifying agents. The invention further relates to aqueous dispersions comprising isomalt, and an opacifying agent such as calcium carbonate and/or starch, methods of preparing the same by dispersing the film coating composition materials (system) in ambient temperature water, as well as orally-ingestible substrates film coated with the coatings described herein as well as methods of coating the substrates with the aqueous dispersions.

In one aspect of the invention, there are provided dry powder film coating compositions for the pharmaceutical, nutritional and related arts. The dry powder film coating compositions include isomalt, an opacifying agent such as calcium carbonate and/or starch and/or fine particle size grades of MCC, a water-soluble polymer, and optional ingredients including a plasticizer, glidants, pigments, and other additives commonly used in film coating formulations.

In another aspect of the invention, there are provided aqueous dispersions of the film coating compositions described above that are prepared in ambient temperature water. The dispersions preferably contain from about 5 to about 30% non-water ingredients content. Still further aspects include the coated substrates prepared from the aqueous dispersions.

Yet a further aspect of the invention are methods of increasing the opacity of titanium dioxide free film coatings found on orally ingestible substrates. The methods include dry blending or combining the film coating ingredients, e.g., film forming polymer, etc., which also contain an opacifying amount of calcium carbonate and/or starch with an amount of isomalt sufficient to enhance the opacity of the film coating after it is applied to the orally-ingestible substrate, forming an aqueous dispersion of the resultant dry blended film coating ingredients containing the isomalt and applying the dispersion to an orally ingestible substrate until a desired weight gain is obtained.

In a preferred aspect of this invention, film coatings comprising isomalt, and calcium carbonate and/or starch, are prepared that, when coated onto orally-ingestible substrates, have high opacity, as indicated by a lightness value (L*) that is higher than that of comparable coating formulations without isomalt. In many embodiments, the film coatings on the oral substrates will have a lightness value (L*) of at least about 85, and, in the case of certain film coatings containing isomalt and calcium carbonate, (L*) values of 90 or greater.

The coated ingestible substrates have a visually attractive appearance, free from cracks, pick marks and other surface defects. This combination of properties for a coating system is clearly advantageous over the prior art and existing marketed products. The inventive film coatings can be formulated to be titanium dioxide-free, substantially free of titanium dioxide, i.e. less than 0.5% by wt., or with substantially reduced amounts of titanium dioxide commonly found in dry film coating compositions, e.g. 20-30% w/w, thus providing the artisan with a useful alternative to currently-available film coatings having high degrees of opacity and which are largely dependent upon titanium dioxide for achieving that result.

DETAILED DESCRIPTION OF THE INVENTION

For purposes of the present invention, the following terms are given further clarification as to their meanings:

- "orally-ingestible substrate" shall be understood to mean any pharmaceutically acceptable dosage form, e.g. tablet, capsule, caplet, etc. or any other veterinary, nutritional or confectionary product intended to be swallowed;
- "dry powder" shall be understood to mean powders which are relatively dry to the touch rather than powders which are essentially without liquid content;
- "ambient temperature" shall be understood to mean temperatures generally in the range of from about 20° C. (68° F.) to about 30° C. (86° F.)+/−3° C.;
- "glycerin" is synonymous with "glycerol", and "glycerol esters" is synonymous with glycerides;

"fully formulated" as it relates to film coating systems shall be understood to include dry powder mixtures or aqueous dispersions containing all of the components necessary for film coating an orally ingestible substrate such as a compressed tablet in a manner consistent with good manufacturing practice (GMP) in the pharmaceutical and nutritional supplement industries; and "fine particle size grades" as used in the description of microcrystalline cellulose (MCC) shall be understood to describe MCC grades in which 99% or more of the MCC particles have a particle size of about 45 microns or less. For purposes of the description of the invention, "MCC" when used herein shall be understood to refer to microcrystalline celluloses having the fine particle size grade characteristics.

The inventive film coating compositions can comprise a water-soluble polymer, isomalt, opacifying agent such as calcium carbonate and/or starch and/or MCC, and optionally a plasticizer, glidants, pigments, surfactants and other film coating auxiliaries.

Preferred water-soluble polymers include polyvinyl alcohol (PVA), polyvinyl alcohol-polyethylene glycol graft copolymer (e.g. Kollicoat IR), hydroxypropyl methylcellulose (HPMC) and hydroxypropyl cellulose (HPC). Preferred grades of HPMC are lower viscosity grades such as those with aqueous solution viscosities of 1, 3, 6, 15 and 50 centipoise (cP) when dissolved at 2% weight/volume in water. Preferably, these water-soluble polymers are of sufficiently small particle size, preferably less than 250 microns, to facilitate dissolution into ambient water when forming the aqueous coating solutions. These polymers may be used alone or together. In most embodiments, the amount of water-soluble polymer(s) included in the powder mixtures of the present invention is from about 25 to about 50% by weight. In some preferred embodiments, it ranges from about 30 to about 40%.

A plasticizer is used to help to aid in film formation and is included in many embodiments of the invention. Preferred plasticizers are those known to plasticize water-soluble polymers and include polyethylene glycol, glycerin, triacetin, medium chain triglycerides, and sunflower oil. The amount of plasticizer, when present, will depend upon need, but can broadly range from about 0.1 to about 10% by weight in the powder mixtures. Preferably, the range is from about 2 to about 10%. Advantageously, polyvinyl alcohol-polyethylene glycol graft copolymer is internally plasticized and often does not require the additional plasticizers such as polyethylene glycols. Plasticizers may be optional when other water-soluble polymers are used as well depending on the nature and quantity of other formulation components. As such, there are embodiments of the invention wherein the film coating compositions are not only titanium dioxide free but also plasticizer free.

An opacifying agent enhances the hiding power of a film coating such that the color of the underlying substrate is not visualized, allowing the intended color of the coating alone to be observed. Preferred opacifying agents are those which have maximal hiding power. Some preferred opacifying agents are insoluble in water and have fine particle sizes with greater that 99% of the particles being less than about 45 microns. Preferred opacifying agents include calcium carbonate, starches and fine particle size grades of microcrystalline cellulose. Among starches, rice starch is more preferred.

For purposes of the present invention, the calcium carbonate and/or starch and/or MCC portion of the inventive film coating compositions is/are referred to herein as opacifying agents or as an opacifier to provide hiding power to the film coating formulation. Opacity increases with increasing opacifying agent concentration. In some embodiments, the opacifying agent is calcium carbonate and the amount of calcium carbonate included in the powder mixtures of the present invention is an amount which is sufficient to provide a measurable increase in the opacity of the film coating after application to the orally-ingestible substrate. For example, an amount of opacifying agent from about 25 to about 50% by weight is suitable for most aspects of the invention. In some preferred embodiments, it ranges from about 30 to about 40%.

Alternatively, starch is used in the film coatings of the invention as an opacifying agent in amounts the same as that set forth above with respect to the calcium carbonate. Starch may be derived from any of a variety of botanical sources including rice, corn, wheat, potato, tapioca and pea. Starch opacifying agents may be unmodified or modified by physical and/or chemical processing. High purity grades of said starches, meeting global pharmacopeial specifications, are preferred. Rice starch meeting United States Pharmacopeia-National Formulary (USP-NF), European Pharmacopoeia (PhEur) and Japanese Pharmacopoeia (JP) specifications is especially preferred. Similarly, MCC, when used as the opacifying agent will also be present in the same amounts as other opacifying agents. Blends of the various opacifying agents, such as combinations of calcium carbonate and starch and/or MCC are also contemplated wherein the total amount of the opacifying agent, within the ranges provided above, is comprised of varying ratios of the calcium carbonate, starch and MCC.

Isomalt is used as a binder and opacity enhancer. Preferred grades of isomalt are those which comply with global compendial specifications including USP-NF, PhEur, JP and FCC specifications. Preferred grades of isomalt also exist in an agglomerated state; wherein, relatively small particles of less than about 60 microns account for less than 15% by weight of the isomalt. While not wishing to be bound by any particular theory, it is believed that isomalt tightly binds and orients the opacifying agent particles during the film formation process on the surface of an orally-ingestible substrate such that the opacity of the coating is higher than when isomalt is not included.

The amount of isomalt included in the film coating compositions is generally regarded as an amount which enhances the opacity of the film coating and opacifying agents. In preferred aspects of this invention, the isomalt levels are advantageously maintained in the range of about 25 to about 35% by weight, or between 28 and 32% by weight. Decreasing the isomalt concentration below 25% can result in coatings with inferior opacity. By including the isomalt in the amounts described herein, titanium dioxide free film coatings achieve an increase in whiteness as measured by (L*), described in more detail below, of at least about 2% and in many cases at least about 3% or more as compared to film coatings which do not include the same amounts of isomalt. While amounts of isomalt above the preferred levels can be used in some instances, it will be appreciated that using amounts of isomalt above about 40% would lead to corresponding decreases in other formulation components. Decreasing the water-soluble polymer content below about 25% decreases film strength, which could lead to chipping or cracking of the coating applied to the substrates or other defects. Decreasing the content of the opacifying agent below about 25% generally result in undesirable reductions in opacity and L* values.

A glidant is optionally used to help tablets flow over each other and so generate a smooth surface finish. A preferred glidant is talc. The amount of glidant, when present, will depend upon need, but can broadly range from >0 to about 15% by weight in the powder mixtures. Preferably, the range is from about 5 to about 10% by weight.

Pigments are also optionally added and may be any food or pharmaceutically approved colors or dyes. For example, the pigments may be aluminum lakes, iron oxides, titanium dioxide, natural colors, or pearlescent pigments (e.g. mica-based pigments sold under the Candurin trade name). Examples of such pigments are listed in U.S. Pat. No. 4,543,570, which is incorporated herein by reference. When included, the pigments may be used in the powder mixtures in a range (by weight) from about greater than 0 to about 20% pigment and, preferably, from about 1 to about 15%. It will be understood, however, that the amount of pigment employed in the powder mixtures of the invention is an amount which is sufficient or effective to impart the required appearance of the outer coating to the surface of the substrate to be coated while still achieving sufficient opacity.

Furthermore, the powder mixtures may also include supplemental or auxiliary ingredients typically found in film coatings. A non-limiting list of such adjuvants includes surfactants, suspension aids, secondary film formers, sweeteners, flavorants, etc. and mixtures thereof.

The powder mixtures are prepared using standard dry blending or mixing techniques known to those of ordinary skill. For example, the ingredients are individually weighed, added to a suitable apparatus and blended for a sufficient time until a substantially uniform mixture of the ingredients is obtained. The time required to achieve such substantial uniformity will, of course, depend upon the batch size and apparatus used. Addition of liquid plasticizers such as glycerin will occur such that no significant agglomeration or separation will occur. This can be accomplished by gradually adding the liquid to the dry ingredients while blending. A pre-blend may also be utilized, wherein the liquid plasticizers are first added to a portion of the dry ingredients and then the remaining dry material is added. The pre-blend may be prepared in bulk and used as needed to reduce the mixing time required for smaller batches. In all cases, when the liquid plasticizers are added to the dry ingredients, the components must be mixed for a time sufficient to ensure homogeneity.

As mentioned above, batch sizes will vary upon need. A non-limiting list of suitable blending devices include diffusion blenders such as a cross flow, V-blender, or hub blender, available from Patterson-Kelly, or convection blenders, available from Azo and Readco, respectively, may be used. Blending of the aforementioned formulations may also be achieved by processing ingredients into a granular form to produce a non-dusting granular coating composition by methods including, but not limited to, wet massing, fluid bed granulation, spray granulation and dry compaction, roller compaction or slugging. Other manners of blending will be apparent to those of ordinary skill.

Some preferred dry film coating compositions in accordance with the present invention include:

| Ingredient | % by weight |
|---|---|
| Water-soluble polymer | 25-50 |
| Plasticizer | 0-10 |
| Opacifying Agent | 25-50 |
| Isomalt | 25-35 |
| Glidant | 0-15 |
| Pigments | 0-20 |
| Optional or auxiliary ingredients | 0-20 |

It will be understood from the foregoing table that the preferred dry film coating compositions will include a water-soluble polymer or mixtures thereof in the amount of as described herein. The additional ingredients will cause the amount of water-soluble polymer to be reduced proportionally, but all of these components will still be within the ranges described herein, so that the total amount of all ingredients in the dry blend will be 100% by weight.

For purposes of illustration and not limitation, an aqueous dispersion having about 20% non-water ingredients can be formed by dispersing 100 parts of a blended powder mixture described hereinabove into 400 parts of ambient temperature water. The water is weighed into a suitable vessel, i.e. one with a diameter approximately equal to the depth of the final suspension. A low shear mixer, preferably one having a mixing blade with a diameter about one third the diameter of the mixing vessel, is lowered into the water and turned on to create a vortex from the edge of the vessel down to about just above the mixing blade to prevent entrapment of air. The 100 parts of dry film coating composition is added to the vortex at a rate where there is no excessive buildup of dry powder. The speed and depth of the mixing blade is adjusted to avoid air being drawn into the suspension so as to avoid foaming. The suspension is stirred at low speed, preferably 350 rpm or less, for a time sufficient to ensure that a homogenous mixture is formed. Using the above batch size as a guide, about 45 minutes mixing time is required. The suspension is then ready for spraying onto pharmaceutical substrates and the like. Those of ordinary skill will also realize that there are many ways of preparing a substantially homogenous mixture of the solids in water and that the scope of the invention is in no way dependent on the apparatus used. It is contemplated that suitable aqueous dispersions will contain from about 5 to about 30% by weight and preferably from about 15 to about 25% by weight non-water ingredients therein.

In still further embodiments of the invention, there are provided orally-ingestible substrates coated with the inventive film coating formulations. The coated substrates have high opacity, as indicated by a lightness value (L*) greater than that of similar coatings without the amounts of isomalt included in the film coating compositions described herein (L* typically >85 for some isomalt containing formulations, and >90 for other isomalt film coatings made with calcium carbonate as the opacifying agent) and a visually attractive appearance, substantially free from cracks, pick marks and other surface defects.

The invention further includes methods of increasing the opacity of a film coating composition comprising an opacifying agent such as calcium carbonate or starch and which is preferably free of titanium dioxide. The methods generally include:

a) combining the film coating compositions in preferably the dry state with an amount of isomalt sufficient to increase the opacity of the dried film coating after being applied to an oral substrate as an aqueous suspension;

b) preparing an aqueous suspension of the isomalt-containing film coating composition;

c) applying the resultant aqueous suspension to an oral substrate.

Film coating compositions well suited for improvements in opacity include those which contain at least about 20 or 25% by weight of an opacifying agent. The amount of isomalt which is effective to increase the opacity of the film coating after application to the oral substrate to a weight gain of at least about 2% and preferably about 4% is preferably from about 25 to about 35% by weight of the film coating composition. The resultant coated oral substrates preferably have an L* value of 85 or greater and, in preferred aspects where the film coating formulation includes calcium carbonate in an amount of at least about 25% wt, have an L* value of about 90 or higher.

Those skilled in the art will recognize that CIELAB color coordinates are typically used to characterize color. It describes all the colors visible to the human eye and was created to serve as a device-independent model to be used as a reference. The CIELAB color space (also known as CIE L*a*b* is a color space defined by the International Commission on Illumination or French Commission internationale de l'eclairage (CIE) in 1976. It expresses color as three values: L* for the lightness from black (0) to white (100), a* from green (—) to red (+), and b* from blue (—) to yellow (+). CIELAB was designed so that the same amount of numerical change in these values corresponds to roughly the same amount of visually perceived change. For white coatings, the L* value indicates the degree of whiteness.

Whiteness increases with increasing L* values. Maximizing L* values is preferred for white coatings. The lightness value, L* in CIELAB is calculated using the cube root of the relative luminance with an offset near black. This results in an effective power curve with an exponent of approximately 0.43 which represents the human eye's response to light under daylight (photopic) conditions. Therefore, the L* scale is not linear, and small differences or % changes in numerical L* values can actually represent significant differences in whiteness perceived by the human eye. By including the isomalt in the amounts described herein, titanium dioxide free film coatings achieve an increase in whiteness as measured by an L* of at least about 2% or 3% or more as compared to film coatings which do not include the same amounts of isomalt. As such, an L* increase of 2% or 3% can be perceived as a significant increase in whiteness by the human eye.

As will be described in the examples below, the methods include applying the film coating compositions as aqueous suspensions to the surfaces of orally ingestible substrates. The film coating can be applied as part of a pan coating or spray coating process commonly used to coat such articles. The amount of coating applied will depend upon several factors, including the nature and functionality of the film coating, the substrate to be coated and the apparatus employed to apply the coating, etc. In some immediate release applications of the invention, the substrates will be tablets and will be coated to a theoretical weight gain of from about 0.25 to about 5.0%. Preferably, the theoretical weight gain is from about 1.0 to about 4.5% and more preferably, the theoretical weight gain is from about 2.5 to about 3.5% by weight of the substrate. For economic reasons, it is preferred to apply as low a weight gain as possible while obtaining acceptable opacity and overall aesthetic characteristics. As mentioned above, the coating solutions of the present invention may also include auxiliary ingredients in addition to the powder mixture and the water.

The coated, orally-ingestible substrates described above can also include a subcoat film coating between the orally-ingestible substrate and the inventive film coating. The subcoat selected is preferably based on an edible film coating composition that is compatible with and adheres to both the orally ingestible substrate and the inventive coating. Thus, the artisan may choose from a wide variety of pharmaceutical or food-acceptable coatings for use as subcoats in the present invention. The subcoat is also applied to the substrate to provide from about a 0.25 to about a 5.0% weight gain to the orally-ingestible substrate.

Regardless of the method employed or the specific materials included in the film coating compositions, the orally-ingestible substrates of the present invention will include a film coating applied to a weight gain sufficient to obtain acceptable opacity and overall aesthetic characteristics.

EXAMPLES

The following examples serve to provide further appreciation of the invention but are not meant in any way to restrict the effective scope of the invention. All ingredients are expressed as being by weight %.

Example 1

A preferred formulation for an inventive dry coating composition is the following:

| Component | Weight % |
|---|---|
| Calcium carbonate | 35.0 |
| Isomalt | 30.0 |
| HPMC (6 cP grade) | 19.0 |
| HPMC (15 cP grade) | 13.0 |
| Medium chain triglycerides | 3.0 |
| | 100.0 |

Preparation of the Dry Film Coating Composition:

The dry film coating composition was prepared by adding the ingredients into a laboratory blender and blending for 5 minutes until a homogenous mixture was produced.

Preparation of the Aqueous Dispersion:

The dry film coating composition (100 parts) was dispersed into 400 parts of ambient temperature water to make an aqueous coating suspension having 20% w/w non-water ingredients. The water was weighed into a vessel with a diameter approximately equal to the depth of the final dispersion. A low shear mixer was lowered into the water and turned on to create a vortex from the edge of the vessel down to just above the mixing blade to prevent entrapment of air. The 100 parts of dry film coating composition was added to the vortex at a rate where there was no excessive buildup of dry powder or foam. The speed and depth of the mixing blade was adjusted to avoid air being drawn into the suspension so as to avoid foaming. The suspension was stirred at low speed (350 rpm or less) for 45 minutes to form a homogeneous aqueous dispersion suitable for coating.

Coating of Tablets:

Placebo tablets (3.5 kg), previously sub-coated with a black HPMC-based coating, were coated with the aqueous dispersion of Example 1 at a spray rate of 20 grams/min in a Labcoat I (O'Hara Technologies Inc., Canada) outfitted with a 15" fully perforated pan. A theoretical coating weight gain of 3.0% was applied to the tablets. The resulting coated tablets were smooth, non-tacky, and free from cracks or other surface defects. The coating strongly adhered to the tablet surface, and the coated tablets had no visible friability. The black placebo tablets were purposefully selected to challenge the opacification properties of the inventive coating. As the weight gain of the inventive coating was applied, the color of the tablets gradually became white, and, at 3% weight, the tablets appeared totally white. The whiteness of the tablets coated to 3% weight gain were instrumentally analyzed to determine whiteness/lightness as described below.

Determination of Lightness Value (L*): The lightness value (L*) of coated tablets was determined to be 90.9 on a scale of 0-100, where 0 and 100 correspond to the darkest and lightest shades measurable, on a Datacolor reflectance spectrophotometer. A white tile supplied by Datacolor was used as the standard.

Comparative Examples A-C

Comparative formulations were prepared according to the following ratios:

| | Example | | |
|---|---|---|---|
| Component | A Wt % | B Wt % | C Wt % |
| Calcium carbonate | 35.0 | 35.0 | 40.0 |
| Isomalt | | | 20.0 |
| Erythritol | 30.0 | | |
| Xylitol | | 30.0 | |
| HPMC (6 cP grade) | 19.0 | 19.0 | 8.0 |
| HPMC (15 cP grade) | 13.0 | 13.0 | 22.0 |
| Medium chain triglycerides | 3.0 | 3.0 | 10.0 |
| Totals | 100 | 100 | 100 |

The aqueous dispersion preparations and coating processes were conducted in an analogous fashion to that described in Example 1. The lightness values of the tablets coated to 3% weight gain in the Comparative Examples are compared to that of Example 1 in the following table.

| Example | Lightness Value (L*) of Tablets Coated to 3% Weight Gain |
|---|---|
| Example 1 | 90.9 |
| Comparative Example A | 84.4 |
| Comparative Example B | 88.1 |
| Comparative Example C | 86.3 |

The lightness value of the tablets coated with the inventive film coating composition of Example 1 is 90.9, which is significantly higher than that of the Comparative Examples A-C. When two different sugar alcohols (namely erythritol and xylitol) were substituted for isomalt in Comparative Examples A and B, respectively, the lightness values of the coated tablets were significantly lower. In Comparative Example C, the isomalt level was reduced to 20%, and the lightness value of the coated tablets was again significantly lower than that of Example 1 despite an increase in the calcium carbonate level to 40% w/w. Comparison of Example 1 to Comparative Examples A-C clearly show the unique properties of isomalt as a sugar alcohol and the importance of including it at a high enough level to work synergistically with calcium carbonate to improve opacity.

Example 2

A coating formulation using 25% w/w isomalt was formulated as follows:

| Component | Amount (wt %) |
|---|---|
| Calcium carbonate | 35.0 |
| Isomalt | 25.0 |
| HPMC (6 cP grade) | 37.0 |
| Medium chain triglycerides | 3.0 |
| Total | 100 |

The aqueous dispersion preparation and coating process was conducted in an analogous fashion to that described in Example 1. The lightness value of the tablets coated to 3% weight gain was 90.3. The lightness value was not significantly affected by reducing the isomalt concentration in the formula from 30 to 25% in Example 1 vs. Example 2 (90.9 vs. 90.3).

Example 3

A coating formulation using rice starch in place of calcium carbonate as an opacifying agent was formulated as follows:

| Component | Amount (wt %) |
|---|---|
| Rice starch | 35.0 |
| Isomalt | 30.0 |
| HPMC (6 cP grade) | 19.0 |
| HPMC (15 cP grade) | 13.0 |
| Medium chain triglycerides | 3.0 |
| Total | 100 |

The aqueous dispersion preparation and coating process was conducted in an analogous fashion to that described in Example 1. The lightness value of the tablets coated to 3% weight gain was 85.2.

Comparative Example D

A coating formulation using rice starch in place of calcium carbonate as an opacifying agent, but with erythritol in place of isomalt was formulated as follows:

| Component | Amount (wt %) |
|---|---|
| Rice starch | 35.0 |
| Erythritol | 30.0 |
| HPMC (6 cP grade) | 19.0 |
| HPMC (15 cP grade) | 13.0 |
| Medium chain triglycerides | 3.0 |
| Total | 100 |
| Lightness value (L*) of tablets coated to 3% weight gain | 76.8 |

The aqueous dispersion preparation and coating process was conducted in an analogous fashion to that described in Example 1. The lightness value of the tablets coated to 3% weight gain (76.8) was significantly lower than that of Example 3 containing isomalt (L*=85.2).

It is noted that while the inherent opacity of rice starch is lower than that of calcium carbonate, as evidenced by a lower L* value in Example 3 vs. Example 1 (85.2 vs. 90.9), the use of isomalt rather than another sugar alcohol (i.e. erythritol) similarly results in an increased L* value on tablets coated with film coatings containing rice starch.

Example 4

A coating formulation using 25% w/w isomalt was formulated as follows:

| Component | Amount (wt %) |
|---|---|
| Rice starch | 35.0 |
| Isomalt | 25.0 |
| HPMC (6 cP grade) | 37.0 |
| Medium chain triglycerides | 3.0 |
| Total | 100 |

The aqueous dispersion preparation and coating process was conducted in an analogous fashion to that described in Example 1. The lightness value of the tablets coated to 3% weight gain was 85.9. The lightness value was not significantly affected by reducing the isomalt concentration in the formula from 30 to 25% in Example 3 vs. Example 4 (85.2 vs. 85.9).

Example 5

A coating formulation without plasticizer is formulated as follows:

| Component | Amount (wt %) |
|---|---|
| Rice starch | 35.0 |
| Isomalt | 30.0 |
| HPMC (6 cP grade) | 35.0 |
| Total | 100 |

The aqueous dispersion preparation and coating process is conducted in an analogous fashion to that described in Example 1. A coated substrate with acceptable whiteness is obtained.

Example 6

A coating formulation using fine particle size MCC as an opacifying agent was formulated as follows:

| Component | Amount (wt %) |
|---|---|
| Microcrystalline cellulose (99% < 45 microns) | 35.0 |
| Isomalt | 30.0 |
| HPMC (6 cP grade) | 19.0 |
| HPMC (15 cP grade) | 13 |
| Medium chain triglycerides | 3 |
| Total | 100 |

The aqueous dispersion preparation and coating process was conducted in an analogous fashion to that described in Example 1. The lightness value of the tablets coated to 3% weight gain was 85.4.

Examples 7-12

In these examples, the formulations of Examples 1-6 are modified to replace the stated amount of opacifying agent. Aqueous dispersions are made in the same way and are used to coat tablets in the same way to a weight gain of 3% to provide a film coating thereon having enhanced opacity.

| Example | Opacifying Agent | wt % |
|---|---|---|
| 1 | Calcium Carbonate | 35 |
| 7a | Calcium carbonate | 17.5 |
| | Rice starch | 17.5 |
| 7b | Calcium carbonate | 20 |
| | Rice starch | 15 |
| 7c | Calcium carbonate | 15 |
| | Rice Starch | 10 |
| | MCC | 10 |
| 2 | Calcium Carbonate | 35 |
| 8a | Calcium carbonate | 17.5 |
| | Rice starch | 17.5 |
| 8b | Calcium carbonate | 20 |
| | Rice starch | 15 |
| 8c | Calcium carbonate | 15 |
| | Rice Starch | 10 |
| | MCC | 10 |
| 3 | Rice Starch | 35 |
| 9a | Rice Starch | 17.5 |
| | Calcium Carbonate | 17.5 |
| 9b | Rice Starch | 20 |
| | Calcium Carbonate | 15 |
| 9c | Rice Starch | 20 |
| | MCC | 15 |
| 4 | Rice Starch | 35 |
| 10a | Rice Starch | 17.5 |
| | MCC | 17.5 |
| 10b | Rice Starch | 20 |
| | Calcium Carbonate | 15 |
| 10c | Rice Starch | 20 |
| | MCC | 15 |

While there have been described what are presently believed to be the preferred embodiments of the invention, those skilled in the art will realize that changes and modifications may be made thereto without departing from the spirit of the invention. It is intended to claim all such changes and modifications that fall within the true scope of the invention.

What is claimed is:

1. A dry film coating composition comprising:

i) 25-50% by weight of a water-soluble polymer selected from the group consisting of polyvinyl alcohol, polyvinyl alcohol-polyethylene glycol graft copolymer, hydroxypropyl methylcellulose and hydroxypropyl cellulose;

ii) 25-50% by weight of an opacifying agent selected from the group consisting of calcium carbonate, starch, microcrystalline cellulose, and mixtures thereof; and iii) 25-35% by weight of isomalt particles, wherein less than 15% by weight of the isomalt particles have a particle size diameter of less than 60 microns.

2. The composition of claim 1, wherein the opacifying agent is insoluble in water and in-particle form with greater than 99% by weight of the particles having a particle size diameter of less than 45 microns.

3. The composition of claim 1, wherein the opacifying agent is calcium carbonate.

4. The composition of claim 1, wherein the opacifying agent is starch.

5. The composition of claim 4, wherein the starch is rice starch.

6. The composition of claim 1, wherein the opacifying agent is microcrystalline cellulose.

7. The composition of claim 1, wherein the amount of opacifying agent is 30-40% by weight.

8. The composition of claim 1, wherein the amount of isomalt particles is 28-32% by weight.

9. The composition of claim 1, wherein the isomalt particles are in an agglomerated state.

10. The composition of claim 1, wherein the amount of water-soluble polymer is 30-40% by weight.

11. The composition of claim 1, wherein the water-soluble polymer is hydroxypropyl methylcellulose.

12. The composition of claim 1 further including a plasticizer, said plasticizer being present in an amount of 0.1-10% by weight.

13. The composition of claim 12, wherein the amount of the plasticizer is 2-10% by weight.

14. The composition of claim 13, wherein the plasticizer is selected from the group consisting of polyethylene glycol, glycerin, triacetin, medium chain triglycerides, sunflower oil and mixtures thereof.

15. The composition of claim 1, wherein the composition is free of titanium dioxide.

16. The dry film coating composition of claim 1, wherein i) the water-soluble polymer is hydroxypropyl methylcellulose and is present in an amount of 30-40% by weight;

ii) the opacifying agent is calcium carbonate and is present in an amount of 30-40% by weight; and iii) the isomalt particles are present in an amount of 28-32% by weight, said dry film coating composition further comprising a plasticizer, said plasticizer being present in an amount of 2-10% by weight.

17. An aqueous dispersion prepared by mixing the composition of claim 1 in water.

18. An orally-ingestible substrate film coated with the aqueous dispersion of claim 17.

19. The film coated orally-ingestible substrate of claim 18, wherein the film coating is applied to the orally-ingestible substrate to a weight gain of from about 0.5 to about 5%.

20. The film coated orally-ingestible substrate of claim 18 wherein the film coated substrate has high opacity as defined by a lightness (L*) value of at least 85.

21. The coated orally-ingestible substrate of claim 18 wherein the film coated substrate has high opacity as defined by a lightness (L*) value of at least 90.

22. A method of increasing the opacity of a film coating on an orally-ingestible substrate, wherein the film coating comprises a water-soluble polymer, and an opacifying agent, comprising:

a) preparing an aqueous dispersion of the dry blend of claim 1; and b) applying the aqueous dispersion of step a) to an orally-ingestible substrate as a film coating until a weight gain of at least about 0.5% is achieved.

* * * * *